US012318132B2

(12) United States Patent
Lifshitz

(10) Patent No.: US 12,318,132 B2
(45) Date of Patent: *Jun. 3, 2025

(54) SYSTEM AND METHOD FOR TEMPERATURE CONTROL IN IRRIGATED ABLATION

(71) Applicant: BIOSENSE WEBSTER (ISRAEL) LTD., Yokneam (IL)

(72) Inventor: Alexander Lifshitz, Arcadia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,037

(22) Filed: Feb. 24, 2023

(65) Prior Publication Data
US 2023/0210594 A1    Jul. 6, 2023

Related U.S. Application Data

(63) Continuation of application No. 16/377,821, filed on Apr. 8, 2019, now Pat. No. 11,589,918.

(51) Int. Cl.
*A61B 18/12* (2006.01)
*A61B 18/02* (2006.01)
(Continued)

(52) U.S. Cl.
CPC .......... *A61B 18/1492* (2013.01); *A61B 18/02* (2013.01); *A61B 18/1206* (2013.01);
(Continued)

(58) Field of Classification Search
CPC . A61B 18/1492; A61B 18/1206; A61B 18/12; A61B 18/08; A61B 18/082;
(Continued)

(56) References Cited

U.S. PATENT DOCUMENTS 5,688,267 A    11/1997  Panescu
6,558,385 B1    5/2003  McClurken et al.
(Continued)

FOREIGN PATENT DOCUMENTS

CN    103237515 A    8/2013
CN    107028654 A    8/2017
(Continued)

OTHER PUBLICATIONS

Chinese First Office Action and Search Report dated Jul. 3, 2024, for Application No. 202010268335.7, 8 pages.
(Continued)

*Primary Examiner* — Thomas A Giuliani
(74) *Attorney, Agent, or Firm* — Frost Brown Todd LLC

(57) ABSTRACT

A catheter ablation system includes: a catheter probe having distal end including: a temperature sensor; a plurality of irrigation holes; and an ablating electrode; a radiofrequency (RF) heating controller coupled to the catheter probe and configured to supply RF energy to the ablating electrode to control the ablating electrode to emit heat at a target power; an irrigation controller coupled to the catheter probe and configured to supply an irrigation fluid at a continuously adjustable irrigation flow rate through the catheter probe to exit through the irrigation holes; and an operating console having a processor and memory, the memory storing instructions that, when executed by the processor, cause the processor to control the irrigation controller to set the irrigation flow rate based on the target power and a target average temperature.

14 Claims, 14 Drawing Sheets

(51) Int. Cl.
*A61B 18/14* (2006.01)
*A61B 18/00* (2006.01)

(52) U.S. Cl.
CPC .............. *A61B 2018/00029* (2013.01); *A61B 2018/00351* (2013.01); *A61B 2018/00577* (2013.01); *A61B 2018/00648* (2013.01); *A61B 2018/00702* (2013.01); *A61B 2018/00791* (2013.01); *A61B 2218/002* (2013.01)

(58) Field of Classification Search
CPC ................ A61B 18/14; A61B 18/1402; A61B 2018/00636; A61B 2018/1465; A61B 2018/00029; A61B 2018/00351; A61B 2018/00791; A61B 2018/00577; A61B 2018/00648; A61B 2018/00702; A61B 2018/00357; A61B 2018/00375; A61B 2018/00642; A61B 2018/00714; A61B 2018/00744; A61B 2018/00779; A61B 2018/00011; A61B 2018/00005; A61B 2018/00863; A61B 2218/002
USPC ........ 606/32, 34, 38, 40–42, 49; 607/98, 99, 607/101, 102, 104, 105, 113, 115, 116
See application file for complete search history.

(56) References Cited

U.S. PATENT DOCUMENTS

| | | | | |
|---|---|---|---|---|
| 8,974,478 | B2* | 3/2015 | Ross | A61B 17/3211 606/169 |
| 11,589,918 | B2* | 2/2023 | Lifshitz | A61B 18/1492 |
| 2001/0032002 | A1 | 10/2001 | McClurken et al. | |
| 2010/0168736 | A1 | 7/2010 | Wang | |
| 2010/0211070 | A1* | 8/2010 | Subramaniam | A61B 18/1206 606/49 |
| 2011/0130648 | A1 | 6/2011 | Beeckler et al. | |
| 2012/0165812 | A1 | 6/2012 | Christian | |
| 2013/0184696 | A1 | 7/2013 | Fourkas et al. | |
| 2014/0171821 | A1 | 6/2014 | Govari et al. | |
| 2017/0181787 | A1* | 6/2017 | Govari | A61B 18/1492 |
| 2018/0228529 | A1 | 8/2018 | Govari | |

FOREIGN PATENT DOCUMENTS

| | | |
|---|---|---|
| CN | 108201467 A | 6/2018 |
| CN | 108403208 A | 8/2018 |
| CN | 109069006 A | 12/2018 |
| EP | 2204132 A1 | 7/2010 |
| EP | 3375396 A1 | 9/2018 |
| WO | WO 2014/132476 A1 | 9/2014 |

OTHER PUBLICATIONS

Chinese Second Office Action dated Dec. 25, 2024, for Application No. 202010268335.7, 8 pages.
European Extended Search Report and Written Opinion dated Sep. 4, 2020, for Application No. 20168422.2, 8 pages.
Japanese First Office Action dated Oct. 17, 2023, for Application No. 2020-068835, 6 pages.

* cited by examiner

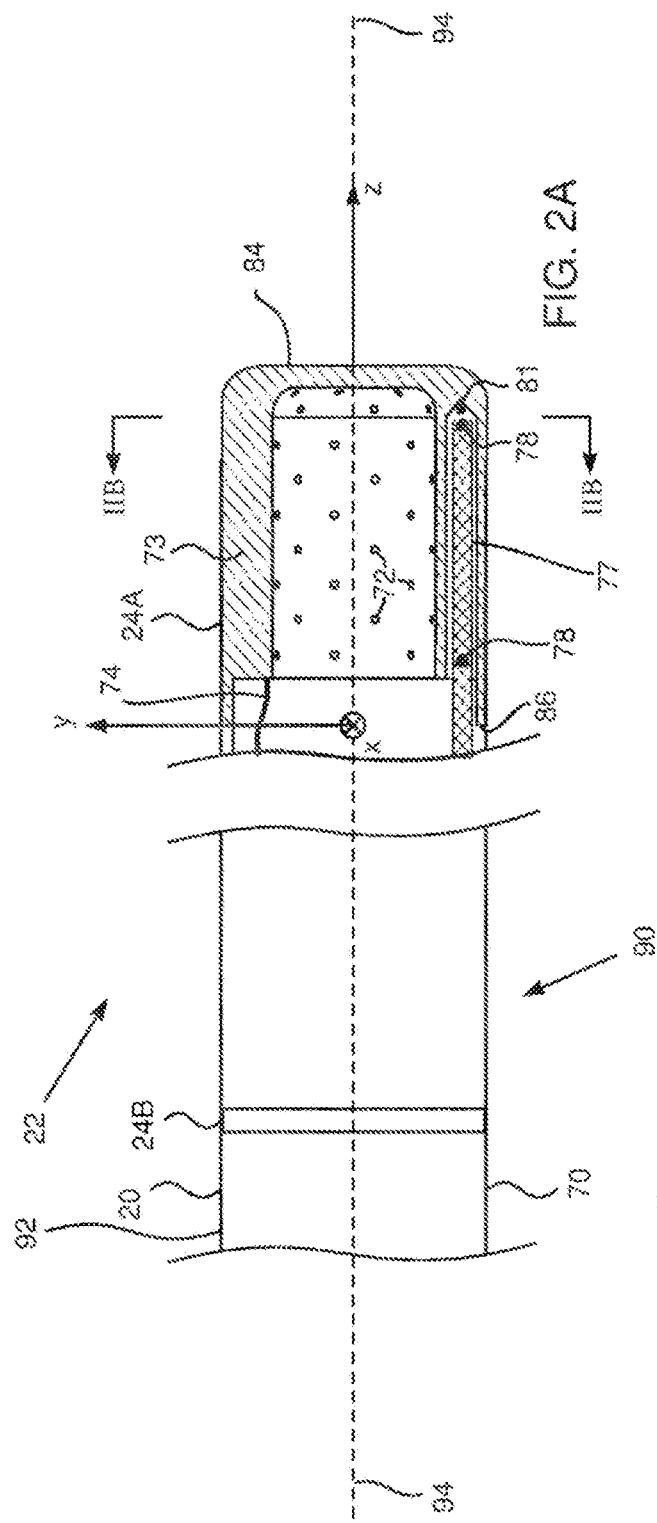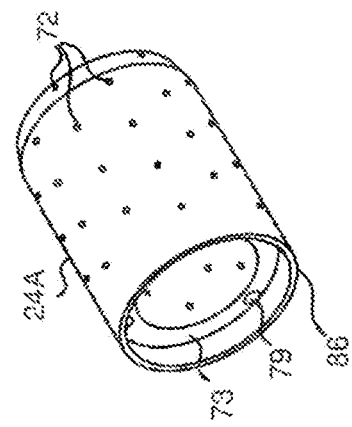

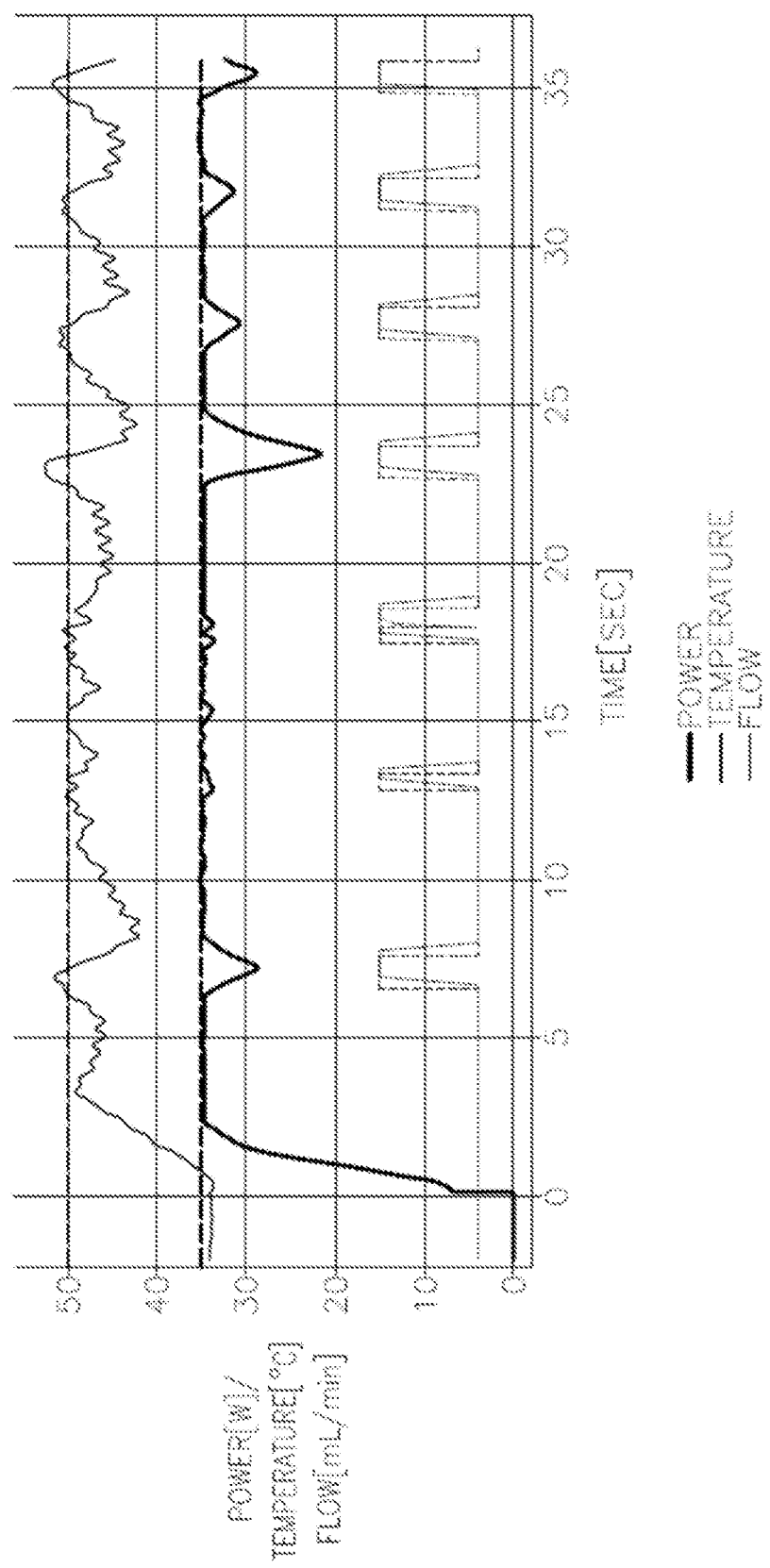

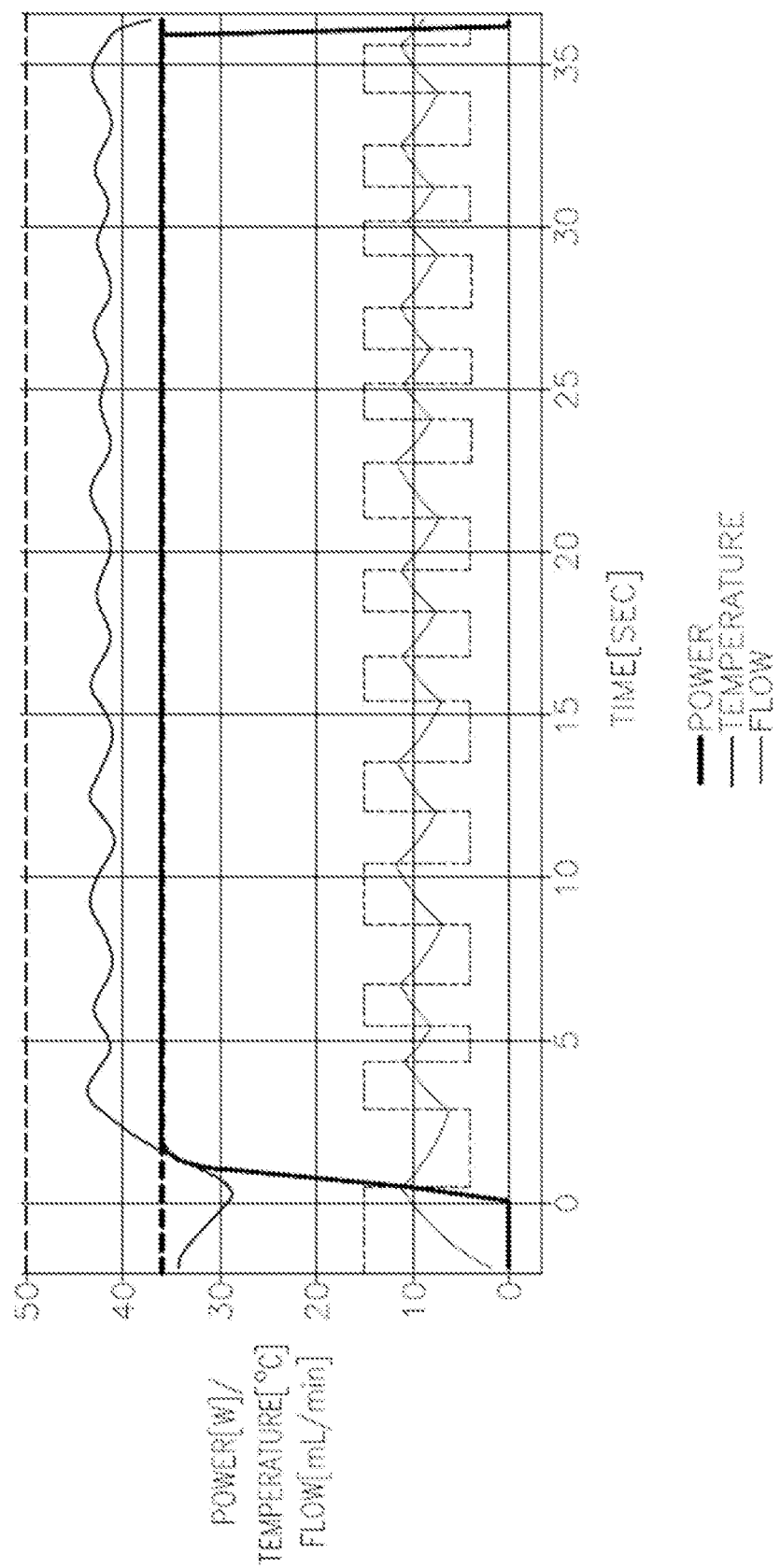

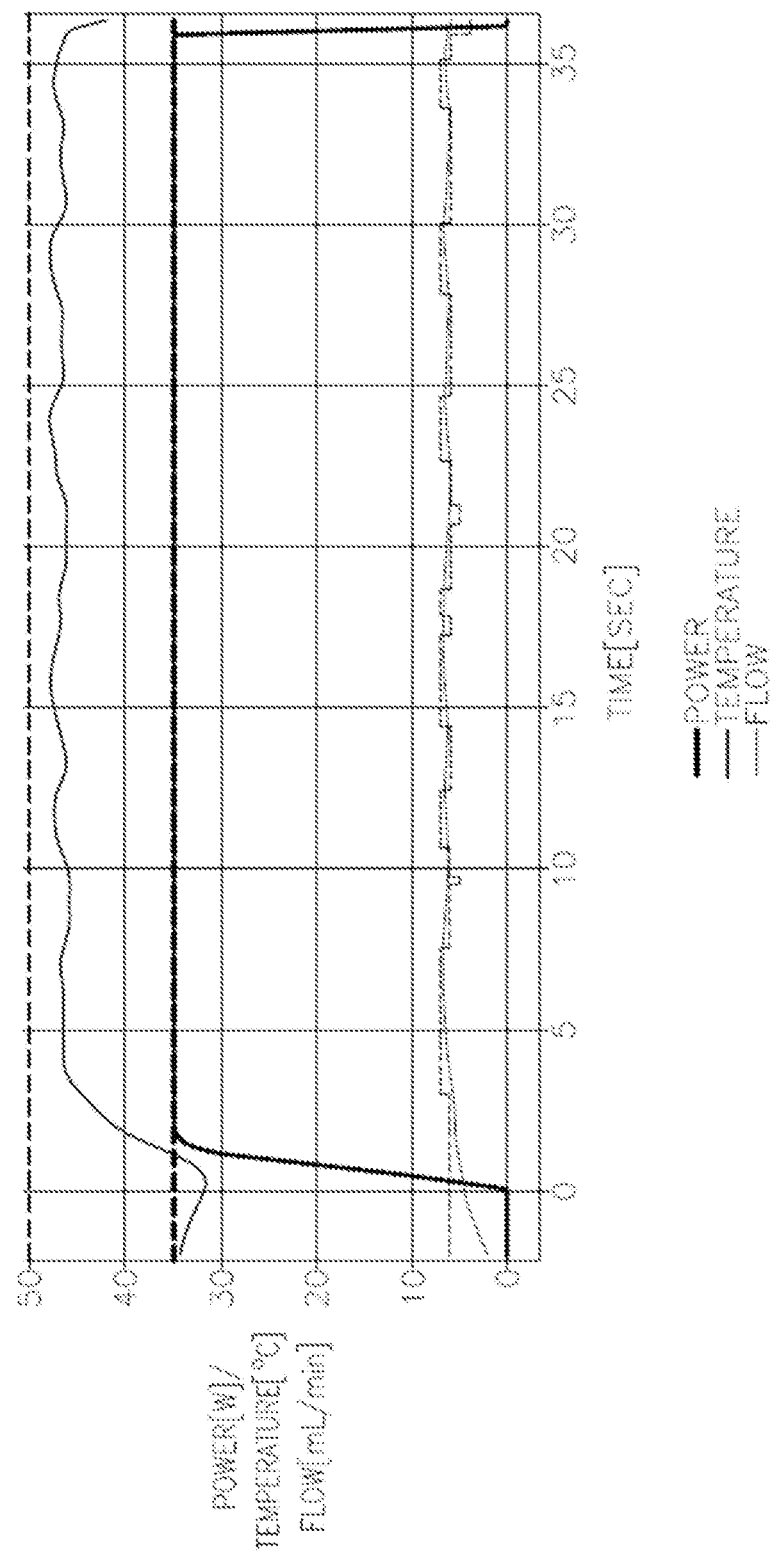

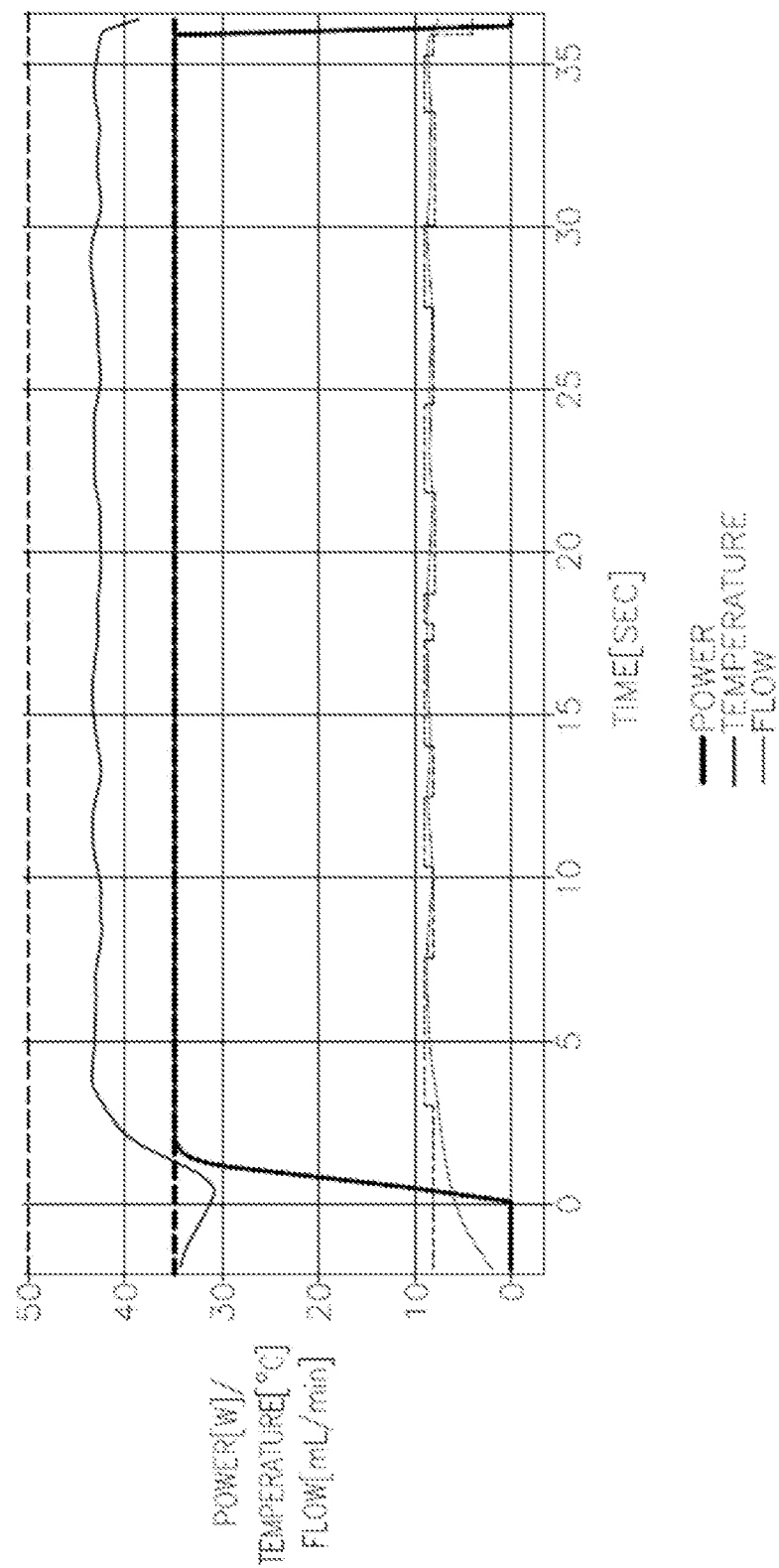

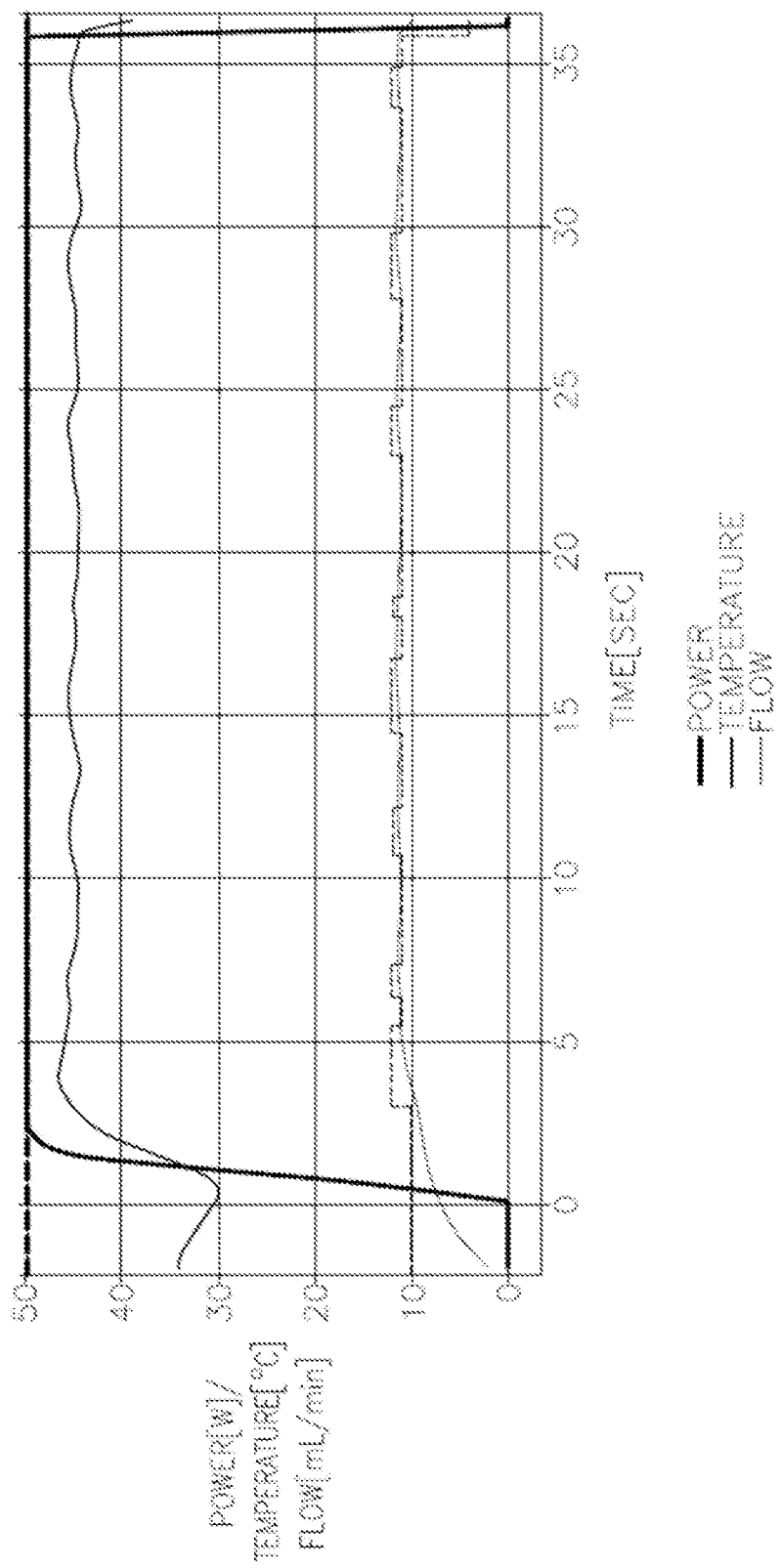

SYSTEM AND METHOD FOR TEMPERATURE CONTROL IN IRRIGATED ABLATION

CROSS REFERENCE TO RELATED APPLICATION(S)

This application is a continuation of and claims priority to and the benefit of U.S. patent application Ser. No. 16/377,821 filed Apr. 8, 2019, now U.S. Pat. No. 11,589,918, the entire content of which is incorporated herein by reference.

FIELD

Aspects of embodiments of the present invention relate to surgery using radiofrequency ablation and systems for performing such surgery.

BACKGROUND

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Electrode catheters have been in common use in medical practice for many years. Diagnosis and treatment of cardiac arrhythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energy to create conduction blocks along the cardiac tissue wall.

In use, the electrode catheter is inserted into a major vein or artery, e.g., the femoral artery, and then guided into a chamber of the heart. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the ablation electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than tissue, impedance to the flow of electrical energy into the tissue also increases. If the impedance increases sufficiently, an impedance rise occurs and the catheter must be removed from the body and the tip electrode cleaned.

In a typical application of RF current, circulating blood provides some cooling of the ablation electrode. Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

RF ablation is typically performed at continuous power levels of the order of 20-50 watts, with a contact force of approximately 10 g, and under irrigation. The time of ablation depends on the size of the lesion to be achieved and is typically approximately 1 minute. In general, higher power levels reduce the time needed for forming a specific lesion. However, large values of continuous power generally cannot be used because of the danger of forming steam pops.

SUMMARY

Aspects of embodiments of the present invention relate to systems and methods for controlling an irrigation pump of an irrigated catheter ablation system. In particular, some aspects of embodiments of the present invention relate to controlling the flow rate of fluid provided to tissues through a catheter probe to control a temperature at a point of contact between a tip of the catheter probe and biological tissue.

According to one embodiment of the present invention, a catheter ablation system includes: a catheter probe having distal end including: a temperature sensor; a plurality of irrigation holes; and an ablating electrode; a radiofrequency (RF) heating controller coupled to the catheter probe and configured to supply RF energy to the ablating electrode to control the ablating electrode to emit heat at a target power; an irrigation controller coupled to the catheter probe and configured to supply an irrigation fluid at a continuously adjustable irrigation flow rate through the catheter probe to exit through the irrigation holes; and an operating console having a processor and memory, the memory storing instructions that, when executed by the processor, cause the processor to control the irrigation controller to set the irrigation flow rate based on the target power and a target average temperature.

The memory of the operating console may further store instructions that, when executed by the processor, cause the processor to control the irrigation controller to set the irrigation flow rate to an irrigation flow rate selected from more than two different irrigation flow rates.

The memory of the operating console may further store instructions that, when executed by the processor, cause the processor to control the irrigation controller to set the irrigation flow rate by a continuously variable amount.

The memory of the operating console may further store instructions that, when executed by the processor, cause the processor to control the irrigation controller to set the irrigation flow rate to a value within a continuous range.

The memory of the operating console may further store instructions that, when executed by the processor, cause the processor to control the irrigation controller to set the irrigation flow rate to an initial irrigation flow rate during a preablation time based on the target power and the target average temperature.

The memory of the operating console may further store instructions that, when executed by the processor, cause the processor to control the irrigation controller to set the irrigation flow rate to an adjusted flow rate during a power ramp up period after the preablation time, the adjusted flow rate being set based on: the target power; the target average temperature; the initial irrigation flow rate; a temperature slope during the preablation time, measured by the temperature sensor; a temperature slope during the power ramp up time, measured by the temperature sensor; and a temperature rise measured since the start of ablation, measured by the temperature sensor.

The memory of the operating console may further store instructions that, when executed by the processor, cause the processor to control the irrigation controller to set the irrigation flow rate using a proportional-integral-derivative control loop based on a current temperature measured by the temperature sensor and the target average temperature.

The target average temperature may be constant with respect to the target power.

The target average temperature may be set to increase linearly with respect to the target power.

According to one embodiment of the present invention, a method for controlling a catheter ablation system including: a catheter probe having distal end including: a temperature sensor; a plurality of irrigation holes; and an ablating electrode; a radiofrequency (RF) heating controller coupled to the catheter probe and configured to supply RF energy to the ablating electrode to control the ablating electrode to emit heat at a target power; and an irrigation controller coupled to the catheter probe and configured to supply an irrigation fluid at a continuously adjustable irrigation flow rate through the catheter probe to exit through the irrigation holes, includes: receiving, by an operating console, the target power and the target average temperature, the operating console being configured to receive signals from the temperature sensor and to control the RF heating controller and the irrigation controller; and controlling, by the operating console, the irrigation controller to set the irrigation flow rate based on the target power and the target average temperature.

The method may further include controlling the irrigation controller to set the irrigation flow rate to an irrigation flow rate selected from more than two different irrigation flow rates.

The method may further include controlling the irrigation controller to set the irrigation flow rate by a continuously variable amount.

The method may further include controlling the irrigation controller to set the irrigation flow rate to a value within a continuous range.

The method may further include controlling the irrigation controller to set the irrigation flow rate to an initial irrigation flow rate during a preablation time based on the target power and the target average temperature.

The method may further include controlling the irrigation controller to set the irrigation flow rate to an adjusted flow rate during a power ramp up period after the preablation time, the adjusted flow rate being set based on: the target power; the target average temperature; the initial irrigation flow rate; a temperature slope during the preablation time, measured by the temperature sensor; a temperature slope during the power ramp up time, measured by the temperature sensor; and a temperature rise measured since the start of ablation, measured by the temperature sensor.

The method may further include controlling the irrigation controller to set the irrigation flow rate using a proportional-integral-derivative control loop based on a current temperature measured by the temperature sensor and the target average temperature.

The target average temperature may be constant with respect to the target power.

The target average temperature may be set to increase linearly with respect to the target power.

BRIEF DESCRIPTION OF THE DRAWINGS

The accompanying drawings, together with the specification, illustrate exemplary embodiments of the present invention, and, together with the description, serve to explain the principles of the present invention

FIG. 2A is a sectional view along the length of a probe according to one embodiment of the present invention.

FIG. 2B is a cross-sectional view along a cut IIB-IIB that is marked in FIG. 2A according to one embodiment of the present invention.

FIG. 2C is a perspective view of a section of the distal end of a probe according to one embodiment of the present invention.

FIG. 3A is a graph illustrating temperature, power, requested irrigation flow rate, and actual irrigation flow rate over time in an animal study using an irrigated catheter ablation system with a comparative irrigation pump controller in a first mode of operation.

FIG. 3C is a graph illustrating simulated temperature, power, requested irrigation flow rate, and actual irrigation flow rate to match the animal study data using an irrigated catheter ablation system with a comparative irrigation pump controller of FIG. 3A in a second mode of operation.

FIGS. 7A, 7B, and 7C are graphs illustrating the simulated performance of irrigation control methods according to embodiments of the present invention.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein.

Figure 1A:
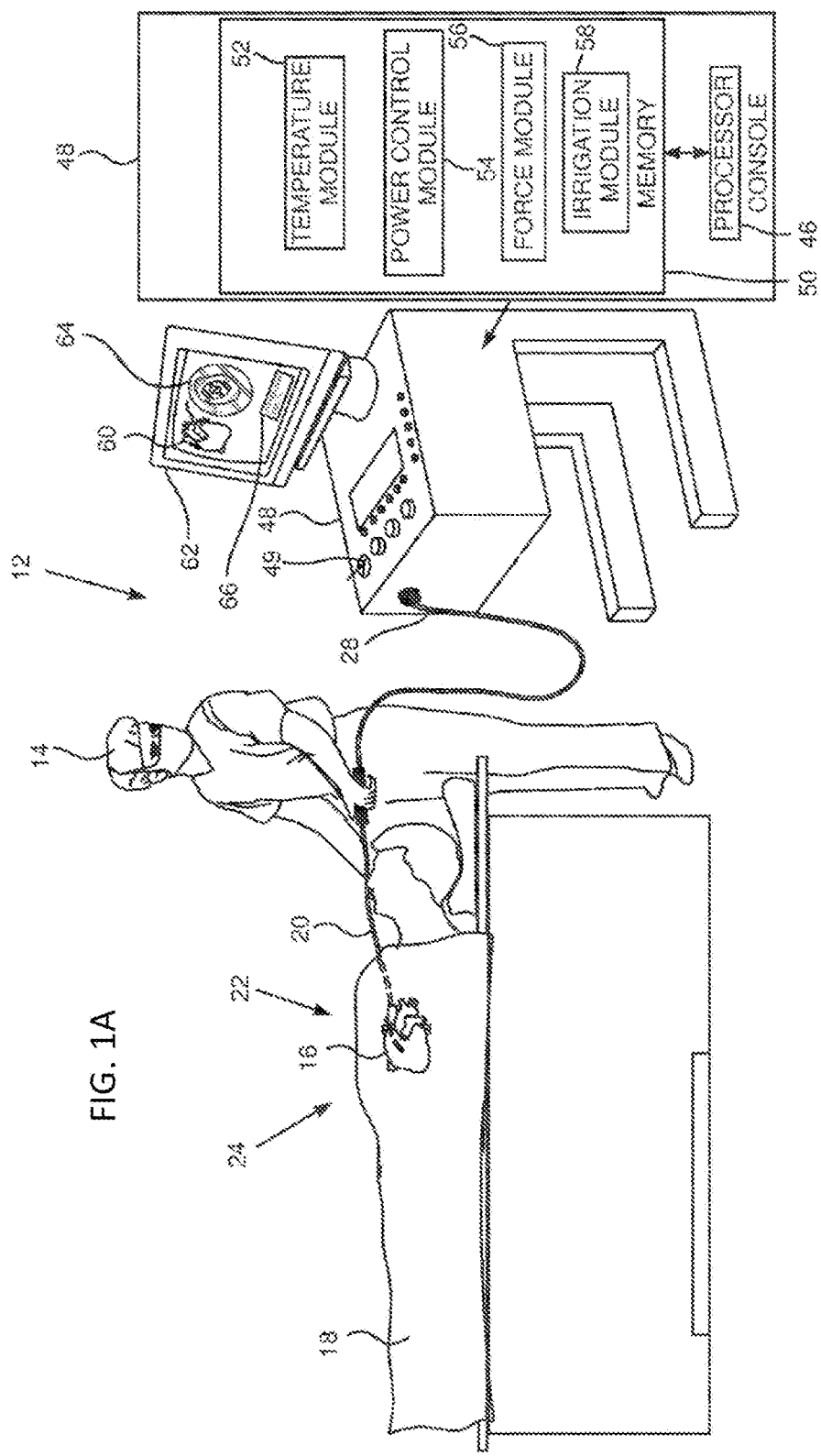
FIG. 1A is a schematic illustration of an invasive medical procedure using an ablation apparatus, according to an embodiment of the present invention.

FIG. 1A is a schematic illustration of an invasive medical procedure using an ablation apparatus 12, according to an embodiment of the present invention. The procedure is performed by a physician 14, and, by way of example, the procedure in the description herein below is assumed to involve the ablation of a portion of a myocardium 16 of the heart of a human patient 18. However, it will be understood that embodiments of the present invention are not limited to this specific procedure, and may also apply to substantially any ablation procedure on biological tissue.

In order to perform the ablation, physician 14 inserts a probe 20 into a lumen of the patient, so that a distal end 22 of the probe 20 enters the heart of the patient 18. Distal end 22 includes one or more electrodes 24 mounted on the outside of the distal end 22, the electrodes 24 contacting respective locations of the myocardium 16. Probe 20 also has a proximal end 28. Distal end 22 of the probe is described in more detail below with reference to FIGS. 2A, 2B, 2C and 2D.

The ablation apparatus 12 is controlled by a system processor 46, which is located in an operating console 48. The operating console 48 includes controls 49 which are used by physician 14 to communicate with the processor 46. During the procedure, the processor 46 typically tracks a location and an orientation of distal end 22 of the probe 20, using any method known in the art. For example, system processor 46 may use a magnetic tracking method, wherein magnetic transmitters external to the patient 18 generate signals in coils positioned in the distal end 22 of the probe 20. The Carto® system produced by Biosense Webster, Inc. of Diamond Bar, CA, uses such a tracking method.

The software for processor 46 may be loaded to be executed by the processor 46 in electronic form, and can be loaded, for example, from a non-transitory memory within the operating console 48 or from an external source (e.g., over a network). Alternatively or additionally, the software may be provided on non-transitory tangible media, such as optical, magnetic, or electronic storage media. The track of distal end 22 is typically displayed in a graphical representation 60 of the heart of patient 18 on a screen 62, where the graphical representation may be a three-dimensional (3-D) model. The progress of the ablation performed with apparatus 12 is typically also displayed on screen 62, as a graphic 64 and/or alphanumeric data 66.

Figure 1B:
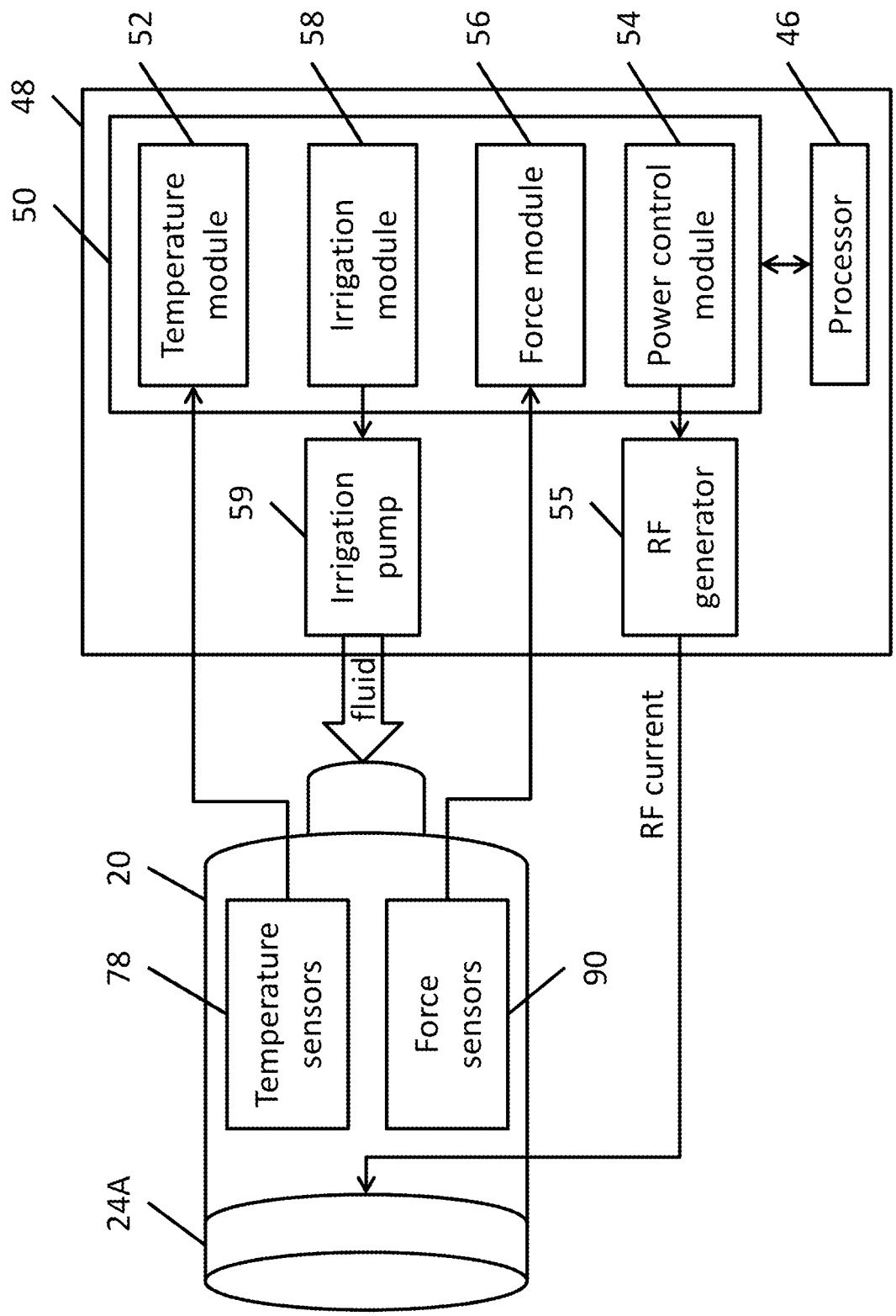
FIG. 1B is a schematic block diagram illustrating components of an ablation apparatus according to one embodiment of the present invention.

FIG. 1B is a schematic block diagram illustrating components of an ablation apparatus according to one embodiment of the present invention. In order to operate apparatus 12, system processor 46 communicates with a memory 50, which stores modules used by the processor 46 to operate the apparatus 48. Thus, the memory 50 includes a temperature module 52, a power control module 54, a force module 56, and an irrigation module 58, the functions of which are described in more detail below. The software modules in memory may be configured to receive data from or control corresponding pieces of hardware of the ablation apparatus 12. For example, the temperature module 52 may be configured to read temperature data from one or more temperature sensors 78 (e.g., thermocouples, thermistors, and the like) at the distal end 22 of the probe 20. The force module 56 may be configured to read force data from sensors in the distal end 22 of the probe 20. The power control module 54 may be configured to control an RF generator 55 to control the radiofrequency power (e.g., radiofrequency current) supplied to myocardial tissue 16 through an ablating electrode 24A). The irrigation module 58 may be configured to control an irrigation pump 59 to deliver fluid (e.g., saline, heparin, or other diagnostic and therapeutic fluids such as neuroinhibitors and neuroexcitors) to the patient's tissues (e.g., myocardial tissue 16) through the probe 20.

The temperature sensors 78 on the distal end 22 of the probe 20 provide feedback to the physician 14 (e.g., via the screen 62) regarding the quality of the contact between an ablating electrode 24A (described in more detail below) at the distal tip of the probe 20 and myocardial tissue 16. Detecting the temperature using the temperature module 52 also allows the processor 46 to control the RF generator 55 based on the temperature.

For example, in some embodiments, the ablation apparatus 12 is operated in a mode of operation where the physician sets a power (e.g., 30 W), and the temperature module 52 implements a safety feature where the processor 46 controls the RF generator 55 (through the power control module 54) to stop delivering power when the temperature module 52 detects that the temperature at the tip has exceeded a threshold value, thereby avoiding or reducing the likelihood of overheating the myocardial tissue 16. As another example, in some embodiments, the ablation apparatus 12 can be operated in a mode where the physician sets a target temperature and the detected temperature is used to increase or decrease the power output by the RF generator 55 (subject to a maximum power) to maintain a constant temperature.

As noted above, the irrigation module 58 is also used to control an irrigation pump 59 to deliver fluid (e.g., saline) to the patient's tissue. The fluid supplied by the irrigation flows through irrigation holes at the distal end of the tip, thereby cooling the tip (e.g., distal end 22) of the probe 20, thereby reducing the chance of overheating and conducting heat to the patient's tissue. The fluid also cools the surface of the patient's tissue, thereby reducing charring and other adverse effects of excessive heating.

Existing techniques for controlling irrigation flow rates are relatively discrete (e.g., binary). One comparative irrigation control system automatically switches between two pre-set flow rates: a low rate (e.g., 2 mL per minute) and a high flow rate (e.g., 17 mL per minute or 30 mL per minute). The switching may be controlled automatically based on conditions such as the output power of the RF generator 55.

The optimal rate of flow depends on characteristics of the tissue, such as the thickness of the tissue. For example, in the case of thin tissue, if the flow rate is too high, then the irrigation may cause too much cooling of the tissue, thereby preventing ablation of the tissue and preventing the formation of an effective lesion to obtain the desired physiological effect of the treatment. On the other hand, in the case of very thick tissue, the same flow rate may be insufficient to cool the tip. This can cause the tip to overheat (e.g. temperature at the tip exceeds a threshold), thereby causing the processor 46 to control the RF generator 55 to reduce output, which also causes insufficient heat to be delivered to the tissue to perform the ablation.

However, these comparative irrigation control systems can result in instabilities (e.g., fluctuating temperatures) and can behave in ways that are unintuitive to physicians, as described in more detail below.

Accordingly, aspects of embodiments of the present invention relate to systems and methods for controlling irrigation flow rates in accordance with ablation conditions, as described in more detail below.

Figure 2D:
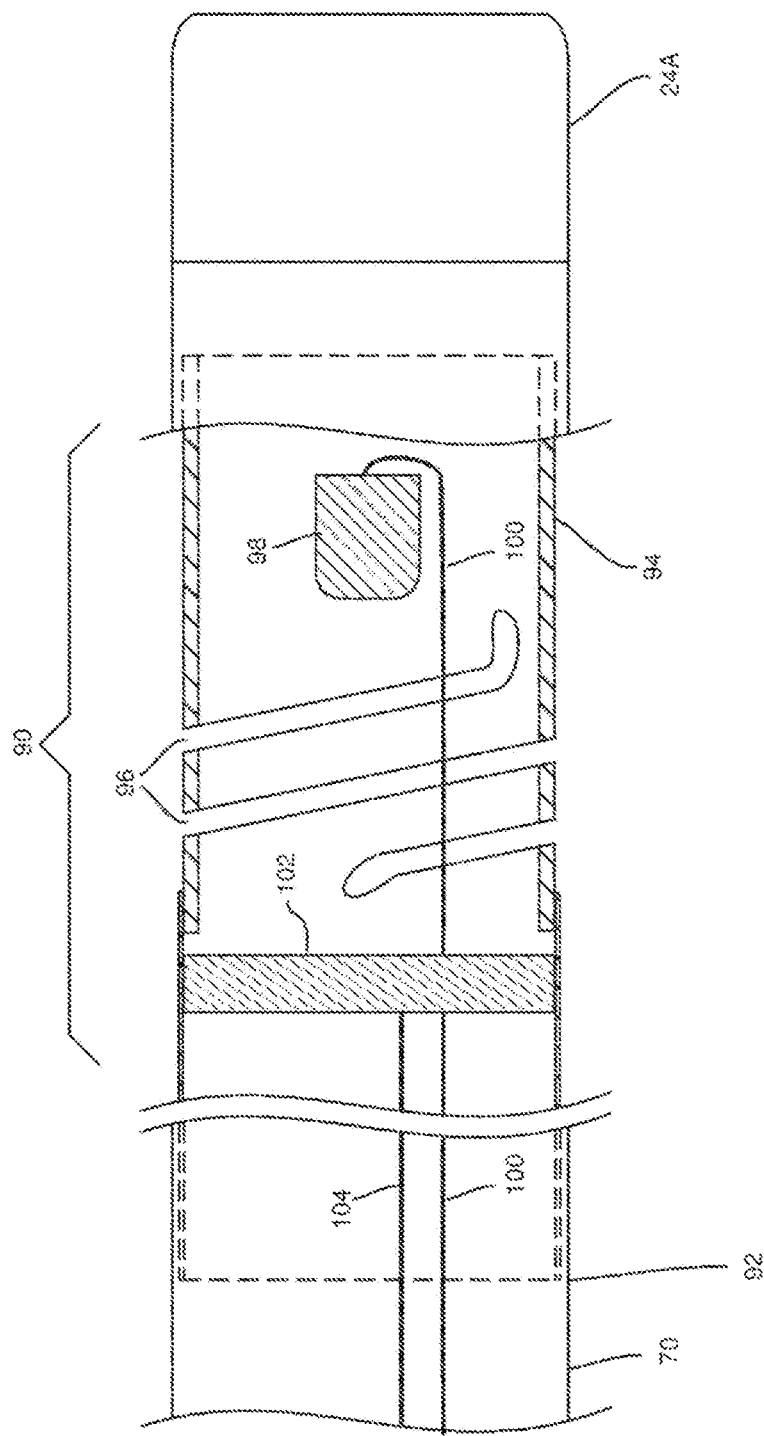
FIG. 2D is a schematic cross-sectional view of a force sensor incorporated into a proximal portion of the distal end of a probe according to one embodiment of the present invention.

Aspects of embodiments of the present invention may be implemented in irrigated ablation catheter systems that include a probe or catheter body 20 having a distal end 22 that is inserted into a patient. FIGS. 2A, 2B, 2C, and 2D schematically illustrate distal end 22 of a probe 20, that is suitable for use with an ablation system 12 according to an embodiment of the present invention. However, embodiments of the present invention are not limited to use with probes having the particular structures depicted in FIGS. 2A, 2B, 2C, and 2D, but instead can be applied to other irrigated ablation catheters. FIG. 2A is a sectional view along the length of the probe 20, FIG. 2B is a cross-sectional view along a cut IIB-IIB that is marked in FIG. 2A, FIG. 2C is a perspective view of a section of the distal end 22 of the probe 20 and FIG. 2D is a schematic cross-sectional view of a force sensor 90 incorporated into a proximal portion 92 of the distal end 22.

With reference to FIGS. 2A and 2B, the probe or catheter body 20 comprises an elongated tubular construction having a single, axial or central lumen. The catheter body 20 is flexible, i.e., bendable, but substantially non-compressible along its length. The catheter body 20 can be of any suitable construction and made of any suitable material. For example, an outer wall of the catheter body may be made of polyurethane or PEBAX. The outer wall may include an imbedded braided mesh of stainless steel or the like to increase torsional stiffness of the catheter body 20 so that, when a control handle attached to the catheter body is rotated, the intermediate section of the catheter 20 will rotate in a corresponding manner.

An insertion tube 70 extends along the length of the probe 20 and is connected at the termination of its distal end 22 to a conductive cap electrode 24A, which is used for ablation. Conductive cap electrode 24A is also referred to herein as an ablation electrode. The conductive cap electrode 24A has an approximately plane conducting surface 84 at its distal end and a substantially circular edge 86 at its proximal end. Proximal to ablation electrode 24A there are typically other electrodes such as an electrode 24B. Typically, insertion tube 70 includes a flexible, biocompatible polymer, while electrodes 24A, 24B include a biocompatible metal, such as gold or platinum. Ablation electrode 24A is typically perforated with irrigation apertures or irrigation holes 72. In one embodiment there are thirty-six (36) apertures 72, distributed evenly over ablation electrode 24A.

An electrical conductor 74 conveys radio-frequency (RF) electrical energy from ablation module 54 (FIG. 1A) through insertion tube 70 to the ablation electrode 24A, and thus the electrical conductor 74 energizes the ablation electrode 24A to ablate myocardial tissue 16 the electrode is in contact with. As described in more detail below below, power control module 54 controls the level of RF power (e.g., wattage) supplied from the RF generator 55 to the ablation electrode 24A. During the ablation procedure, irrigation fluid (e.g., saline) flowing out through irrigation apertures 72 irrigates the tissue (e.g., myocardial tissue 16) under treatment, and the rate of flow of fluid is controlled by irrigation module 58. The irrigation fluid is delivered to ablation electrode 24A by a tube within insertion tube 70.

Temperature sensors 78 are mounted within conductive cap electrode 24A at locations that are arrayed around the distal tip of the probe 20, both axially and circumferentially. In one embodiment, conductive cap electrode 24A includes six temperature sensors, with one group of three temperature sensors in a distal location, close to the tip, and another group of three temperature sensors in a slightly more proximal location. This distribution is shown as an example and greater or fewer numbers of sensors may be mounted in any suitable locations within the conductive cap electrode 24A. The temperature sensors 78 may be thermocouples, thermistors, or any other suitable type of miniature temperature sensor. Temperature sensors 78 are connected by leads running through the length of insertion tube 70 to provide temperature signals to temperature module 52.

In one embodiment, conductive cap electrode 24A has a side wall 73 that is relatively thick (e.g., on the order of 0.5 mm thick) in order to provide the desired thermal insulation between temperature sensors 78 and the irrigation fluid inside a central cavity 75 of the tip. The irrigation fluid exits cavity 75 through apertures 72. Sensors 78 are mounted on rods 77, which are fitted into longitudinal bores 79 in side wall 73. Rods 77 may be made of a plastic material, such as polyimide, and may be held in place at their distal ends by a glue 81, such as epoxy. U.S. Patent Application Publication Number 2014/0171821, to Govari et al., the entire disclosure of which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of orthogonal axes (e.g., along x-, y-, and z-axes), where an axis 94 of the distal end corresponds to the z-axis of the set. For simplicity and by way of example, the y-axis is assumed to be in the plane of the page, the x-y plane is herein assumed to correspond to the plane defined by circle 86, and the origin of the x-, y-, and z-axes is assumed to be the center of the circle.

FIG. 2D is a schematic, sectional view of force sensor 90, according to an embodiment of the present invention. Sensor 90 includes a spring 94, herein assumed to comprise a plurality of helices 96, connecting cap 24A to proximal end 92. A position sensor 98 is fixed to the distal side of spring 94, and is herein assumed to comprise one or more coils coupled by conductors 100 to force module 56.

An RF transmitter 102, typically a coil, is fixed to the proximal side of spring 94, and the RF energy for the transmitter is provided from force module 56 via conductors 104. The RF energy from the transmitter traverses sensor 98, generating a corresponding signal in conductors 100 of the sensor.

In operation, as force is exerted on cap 24A, sensor 98 moves relative to transmitter 102, and the movement causes a change in the signals of the sensor (e.g., a change in capacitance). Force module 56 uses the change in signal of the sensor to provide a metric of the force on cap 24A. The metric typically provides the force in magnitude and direction. A more detailed description of a sensor similar to sensor 90 is provided in U.S. Patent Application Publication Number 2011/0130648, the entire disclosure of which is incorporated by reference herein. While FIG. 2D shows a single force sensor, embodiments of the present invention are not limited thereto. For example, in some embodiments, multiple springs 94 with corresponding sensors 98 may be arranged along the axis 94 of the distal end 22 (e.g., along the z-axis) to provide information about the angle of the force applied to the distal end 22.

FIG. 3A is a graph illustrating temperature, power, requested irrigation flow rate, and actual irrigation flow rate over time in an animal study using an irrigated catheter ablation system with a comparative irrigation pump controller in a first mode of operation. As discussed above, a comparative irrigation pump controller has a discrete or binary irrigation flow control, where the irrigation pump is operated in a "low flow" mode (e.g., 4 mL/min in FIG. 3A) and a "high flow" mode (e.g., 15 mL/min in FIG. 3A).

The data shown in FIG. 3A is collected from an irrigation pump controller that is configured to operate in a first mode corresponding to a "low" output power (in this example, less than or equal to 35 W). In this first mode, irrigation is generally provided at a low baseline flow rate of 4 mL/min and temporarily increases the flow rate to the high flow rate 15 mL/min based on detected changes in temperature (as shown in FIG. 3A, the dotted thin line corresponds to the requested flow rate requested by the irrigation module 58 and the solid thin line indicates the actual flow rate output by the irrigation pump 59). For example, at approximately 6 seconds, the measured temperature (shown by the solid medium line in FIG. 3A) exceeds the maximum temperature threshold of 50° C. (shown by the dashed medium line in FIG. 3A). Accordingly, the irrigation pump temporarily changes the flow rate to the high flow rate (15 mL/min) for about 1 second. In the circumstances shown in FIG. 3A, the output power (shown by the solid thick line in FIG. 3A) also temporarily drops from the target power of 35 W (e.g., set by the physician, indicated in the graph by the dashed medium line at 35 W) to a minimum of 30 W and returns to 35 W over about 1 second. Similar circumstances in which the pump was temporarily controlled to the high flow rate and in which the RF output power was temporarily reduced in response to exceeding the maximum temperature threshold occur at about 14 seconds, 17 seconds, 23 seconds, 27 seconds, 31 seconds, and 35 seconds.

Figure 3B:
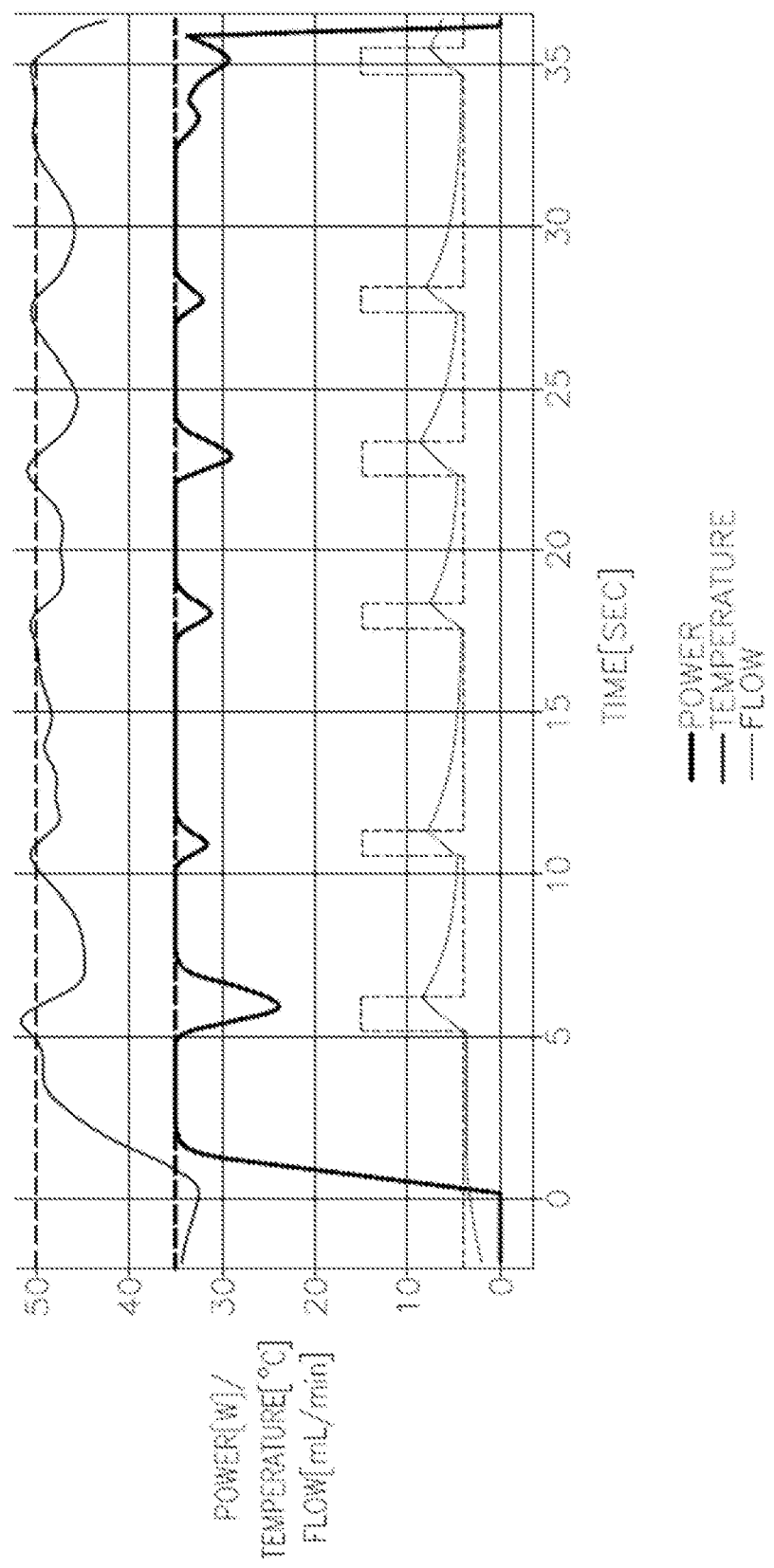
FIG. 3B is a graph illustrating simulated temperature, power, requested irrigation flow rate, and actual irrigation flow rate to match the animal study data using an irrigated catheter ablation system with a comparative irrigation pump controller shown in FIG. 3A in the first mode of operation.

FIG. 3B is a graph illustrating simulated temperature, power, requested irrigation flow rate, and actual irrigation flow rate to match the animal study data using an irrigated catheter ablation system with a comparative irrigation pump controller shown in FIG. 3A in the first mode of operation. As seen in FIG. 3B, the model generally tracks the behavior observed in FIG. 3A for the given combination of a target power of 35 W and a target temperature of 50° C.

In many cases, such as the case shown in FIG. 3A, neither the low flow rate (e.g., 4 mL/min) nor the high flow rate (e.g., 15 mL/min) is the optimal flow rate, thereby resulting in frequent changes in flow rate during ablation and also resulting in unstable temperatures. As seen in FIG. 3A, over the course of the 35 seconds of ablation, although the target temperature is set at 50° C., the actual temperature varies from about 42° C. to about 51° C. This widely varying temperature can affect the quality of the lesions formed, thereby reducing the effectiveness of the ablation system 12.

FIG. 3C is a graph illustrating simulated temperature, power, requested irrigation flow rate, and actual irrigation flow rate to match the animal study data using an irrigated catheter ablation system with a comparative irrigation pump controller of FIG. 3A in a second mode of operation. In this example, the second mode of operation corresponds to a "high" output power (e.g., above 35 W, specifically 36 W in FIG. 3C, as shown by the dotted thick line). When operating in this high output power mode, processor 46 sets the baseline irrigation flow rate to the high flow rate (e.g., 15 mL/min), and temporarily switches to the low flow rate (4 mL/min) when the temperature is below the target value (in this example, 42° C.). As noted before, the optimal flow rate is generally neither 4 mL/min nor 15 mL/min, and this is observed through the frequent switching of flow rates over the course of the approximately 35 second ablation shown in FIG. 3C. As shown in FIG. 3C, the temperature fluctuates (or is unstable) during the course of the ablation, and varies from about 41° C. to about 44° C.

Furthermore, the behavior of the system changes in a way that is non-intuitive to the user (e.g., the physician) because the baseline flow rate switches from the low flow rate to the high flow rate when the physician changes the power setting from a value in the "low power" range to the "high power" range. For example, the flow rate will suddenly change from a low baseline rate to a high baseline rate when changing the RF output power from 35 W to 36 W. This non-linearity in the response of the system is unintuitive, at least because a small change in output power (2 W) would typically be expected to have a small change in system behavior. The main reason here for non-intuitive behavior is that a physician would typically expect that increasing the power would be associated with an increase of the temperature. Here, however, because the default flow is switched from 4 to 15, a physician would actually observe a drop in the average temperature when switching from low power mode to high power mode. Moreover, the temperature behavior is not constant and depends on the force, quality of the contact, tissue thickness, etc. As a result, different ablations may yield different temperature responses, thereby adding to the non-intuitiveness of comparative methods.

As such, aspects of embodiments of the present invention relate to controlling irrigation flow in a way that provides a more predictable temperature response across a range of power and temperature settings, contact force, tissue thickness, and the like, and that also provides more stable temperatures at the catheter tip.

Figure 4A:
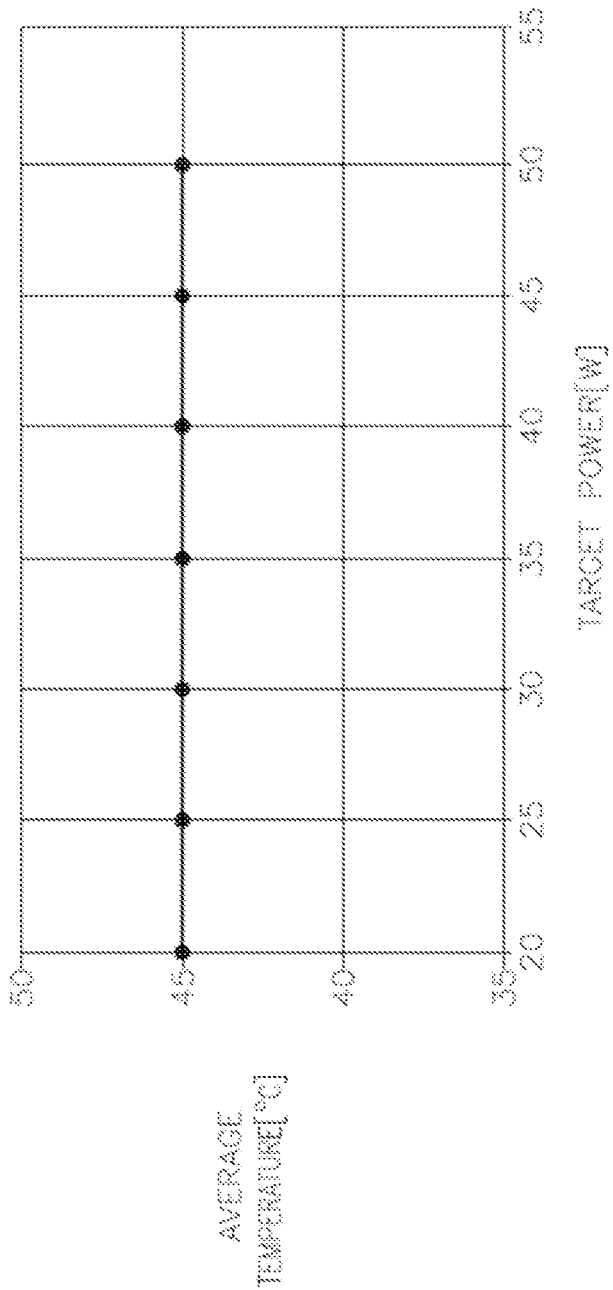
FIG. 4A is a graph illustrating a constant-temperature mode of operation of an ablation system according to one embodiment of the present invention.

Aspects of embodiments of the present invention relate to the use of an irrigation pump 59 that is capable of adjustable flow rate (e.g., continuously adjustable or adjustable in small increments, such as 1 mL/min or smaller), as controlled in real-time or near real-time by the processor 46. This fine-grained control of the flow rate allows the ablation system 12 to achieve various temperature responses, regardless of tissue heat transfer properties, contact force, position of the catheter, and power settings. For example, FIG. 4A is a graph illustrating a constant-temperature mode of operation of an ablation system according to one embodiment of the present invention. As shown in FIG. 4A, embodiments of the present invention are capable of stably maintaining the temperature at a user-supplied (e.g., physician supplied) value across the full RF output power range (e.g., 20 W to 50 W) of the ablation system 12.

Aspects of embodiments of the present invention will be described herein as setting a flow rate to a value in a continuous range. However, embodiments of the present invention are not limited to circumstances in which the flow rate is completely continuously adjustable. As used herein, the term "continuous" includes circumstances in which fine-grained control of the irrigation flow rate is possible (e.g., at a resolution of 1 mL/min). For example, in digitally controlled systems, the flow rate may be specified by an unsigned integer representing the current flow rate in milliliters per minute (mL/min). In the context of this patent application, such digitally controlled systems may still be referred to as providing "continuous" control in view of capability of fine grained control of the irrigation flow rate. However, embodiments of the present invention are not limited thereto and may also include finer resolutions (e.g., 0.5 mL/min or 0.1 mL/min) or slightly coarser resolutions (e.g., 2 mL/min).

Figure 4B:
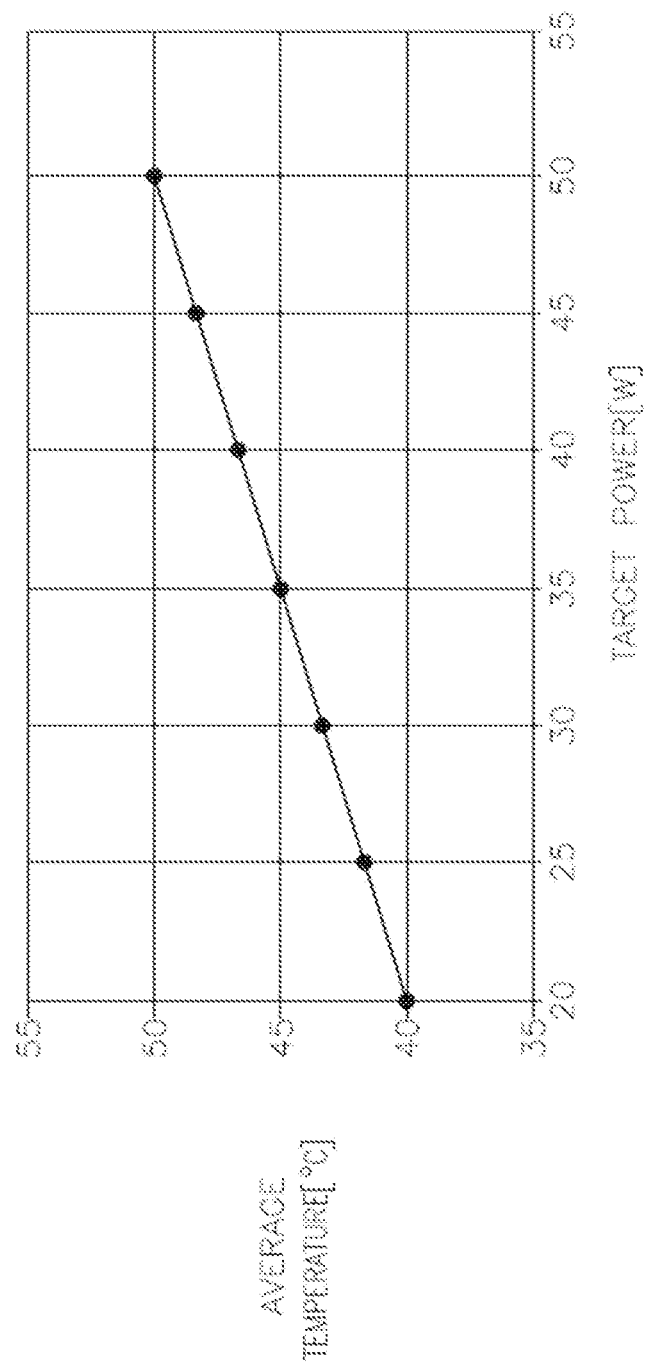
FIG. 4B is a graph illustrating a linearly increasing temperature mode of operation of an ablation system according to one embodiment of the present invention.

FIG. 4B is a graph illustrating a linearly increasing temperature mode of operation of an ablation system according to one embodiment of the present invention. As shown in FIG. 4B, in some embodiments of the present invention, the desired average temperature is defined as a linear function of the target output power (e.g., in FIG. 4B, the average temperature increases linearly from 40° C. to 50° C. as the RF output power increases from 20 W to 50 W).

Figure 5:
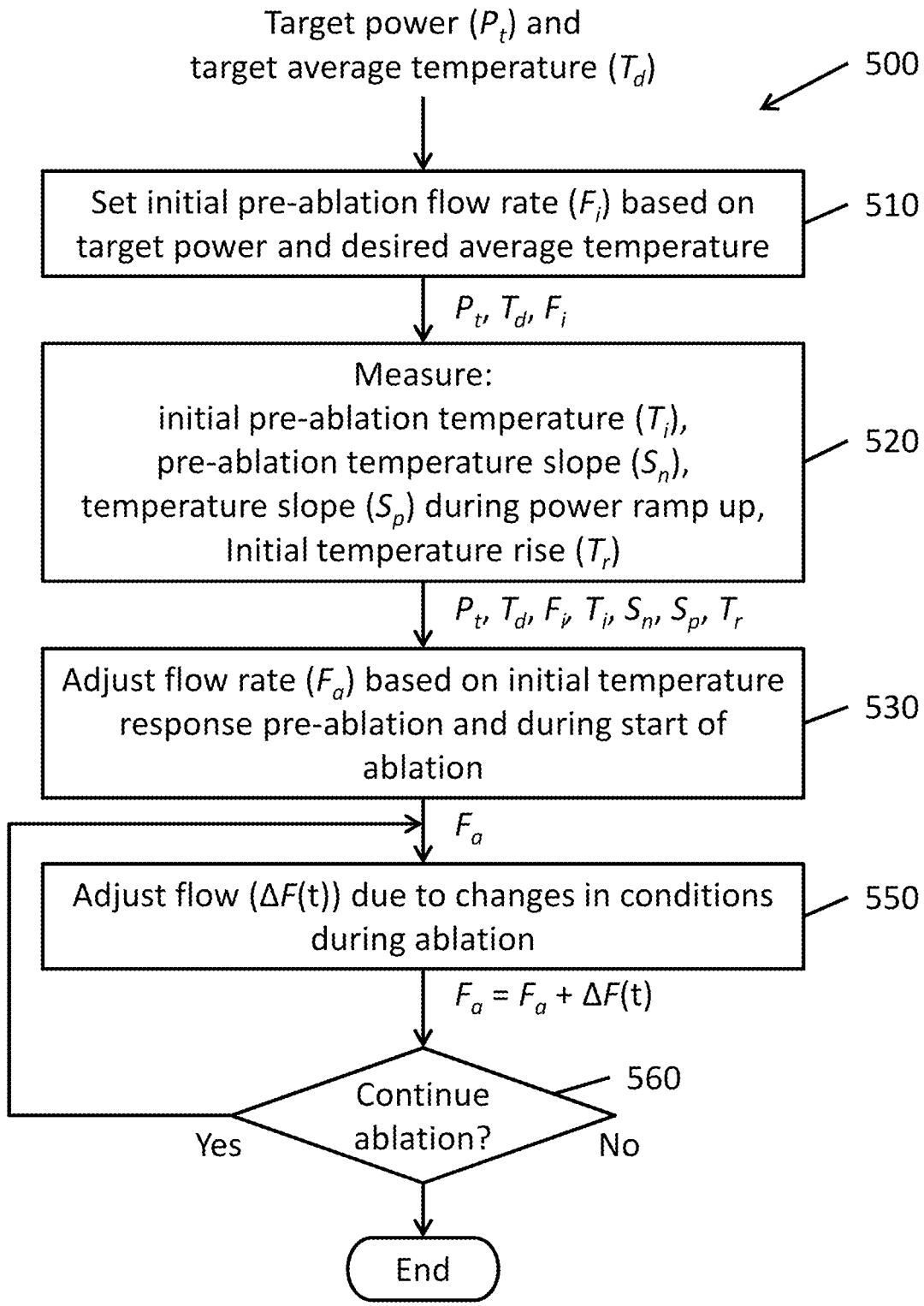
FIG. 5 is a flowchart of a method for controlling an output flow rate according to one embodiment of the present invention.

FIG. 5 is a flowchart of a method 500 for controlling an output flow rate according to one embodiment of the present invention. In operation 510, the irrigation module 58 sets an initial pre-ablation flow rate $F_i$ based on target power and desired average temperature. Starting ablation with an initial flow rate ($F_i$) that is close to the optimal flow rate for a given target power ($P_t$) and target average temperature ($T_d$) reduces or prevents temperature oscillations and allows faster convergence to the desired target temperature. In some embodiments of the present invention, this initial flow rate is supplied as soon as the physician 14 presses the "start" button after setting the target power ($P_t$) and target average temperature ($T_d$). The "start" button is typically pressed about two seconds before the start of ablation to allow effective irrigation at the tip of the catheter. In some embodiments of the present invention, the initial flow rate ($F_i$) is computed as a function of the target power ($P_t$) and target average temperature ($T_d$) ($F_i=f(P_t, T_d)$), where the function f is derived by fitting a regression model against real world data, data generated by a simulation model, or combinations thereof (e.g., real world data augmented by simulation).

In one embodiment of the present invention, relatively accurate predictions of good or optimal initial flow rates are calculated by the regression formula:

$$F_i=48.7+0.2P_t-1.76T_d+0.15T_d^2$$

As a concrete example, the above formula calculates that, for $P_t=50$ W and $T_d=45°$ C., the initial flow rate $F_i=10$ mL/min. For $P_t=30$ W and $T_d=45°$ C., the initial flow rate calculated by the formula is $F_i=6$ mL/min.

After the initial flow rate is set, in operation 520, the temperature module 52 measures the temperature detected by the temperature sensors 78 before ablation (during a "preablation time") as well as during the first few seconds of ablation. These temperature measurements reflect the heat transfer rates of blood and tissues that are specific to the ablation being performed (e.g., the viscosity of the blood and the thickness of the tissue). These temperature measurements include a temperature slope during the preablation time ($S_n$), a temperature slope ($S_p$) during a power ramp up period (e.g., during the period from 1 second after the start of ablation to 2 seconds after the start of ablation), and a temperature rise ($T_r$) measured since the start of ablation (e.g., in the first three seconds).

In operation 530, the irrigation module calculates an adjusted flow ($F_a$) based on the temperature measurements made in operation 520. In some embodiments, this flow adjustment is performed, for example, at three seconds after the start of ablation, during power ramp up, when the temperature has not yet reached its target value and allows the irrigation module to refine the accuracy of the predicted flow rate to match the specific conditions of current ablation to yield a desired average temperature.

In one embodiment of the present invention, relatively accurate predictions of good or optimal adjusted flow rates ($F_a$) are calculated by the regression formula:

$$F_a=23.65-0.028P_t+0.86F_i+2.33S_p+2.12S_n+1.11T_r+\\1.02T_t-2.23T_d+0.015T_d^2-0.033T_r^2+0.08S_n^2$$

In practice, the correction is generally relatively small (e.g., a few mL/min), and, in many cases, is zero. Accordingly, in some embodiments of the present invention, operations 520 and 530 are omitted because the calculated initial flowrate $F_i$ may provide a sufficiently accurate temperature with respect to the desired average temperature $T_d$.

The adjusted flow rate $F_a$ (as well as the initial flow rate $F_i$, in some embodiments) enable the relatively accurate and predictable temperatures. However, in some circumstances, it is possible that the quality of the contact between the catheter tip 22 and the tissue 16 may change during ablation, thereby causing the measured temperature to change. While some physicians use the measured temperature as an indicator of the quality of the contact (e.g., indicating whether the physician needs to adjust the position of the catheter tip to maintain good contact), in some circumstances the physician may find it desirable to maintain a constant temperature even after a change in contact quality.

Accordingly, some aspects of embodiments of the present invention relate to further adjusting the flow rate by applying a proportional-integral-derivative (PID) control loop to control the flow rate based on temperature error with respect to the desired average temperature $T_d$. According to one embodiment of the present invention, in operation 550, the irrigation module 58 calculates a change in the flow $\Delta F$ for a given time t using a low gain, as calculated by the formula:

$$\Delta F(t) = K_p(T - T_d) + K_d \frac{dT}{dt} + K_i \int T - T_d dt$$

After updating the adjusted flow rate $F_a$ based on the change in flow $\Delta F$ to a new flow rate ($F_a=F_a+\Delta F$), the processor 46 determines whether ablation is continuing (e.g., whether the physician is still depressing a trigger for applying RF power to perform the ablation). If so, then the processor 46 returns to operation 550 to continue adjusting the flow (in some embodiments, after a delay, such as 1 second). If ablation is not continuing, then the process for controlling the flow rate ends (e.g., irrigation is stopped or returned to a baseline constant rate).

Therefore, some embodiments of the present invention enable the irrigation module to adjust the fluid flow rate to compensate for large and/or rapid changes in temperature.

Some aspects of embodiments of the present invention relate to systems and methods for simulating tissue temperature response, where such simulations are used to compute the coefficients of the regression models described above with respect to operations 510 and 530. In some embodiments of the present invention, regression models are computed from ablation data that is recorded at a variety of different settings (e.g., power, temperature, and irrigation flow settings) and contact and tissue properties (e.g., thickness, heat capacity, and heat conduction). However, it may be difficult to obtain sufficient real data due to the small number of animal studies that are performed and because, in some circumstances, the only available data come from ablation systems that have irrigation pumps that are configured to deliver fluid at discrete flow rates (e.g., 4 mL/min, 8 mL/min, and 15 mL/min).

Accordingly, some aspects of embodiments of the present invention relate to generating simulated data to generate realistic data for training the regression models. According to one embodiment of the present invention, a tissue temperature model is defined as a function of physical parameters including: tissue mass (volume), which relates to the dissipation of power and which contributes to temperature rise; a tissue heat transfer coefficient (a), which defines a ratio of energy lost to the environment (through heat conduction) and not contributing to temperature rise; and an irrigation cooling efficiency coefficient ($\beta$), which controls the rate at which irrigation contributes to tissue cooling (e.g., may be reflective of tip design, occlusion of irrigation holes, and the like).

Figure 6:
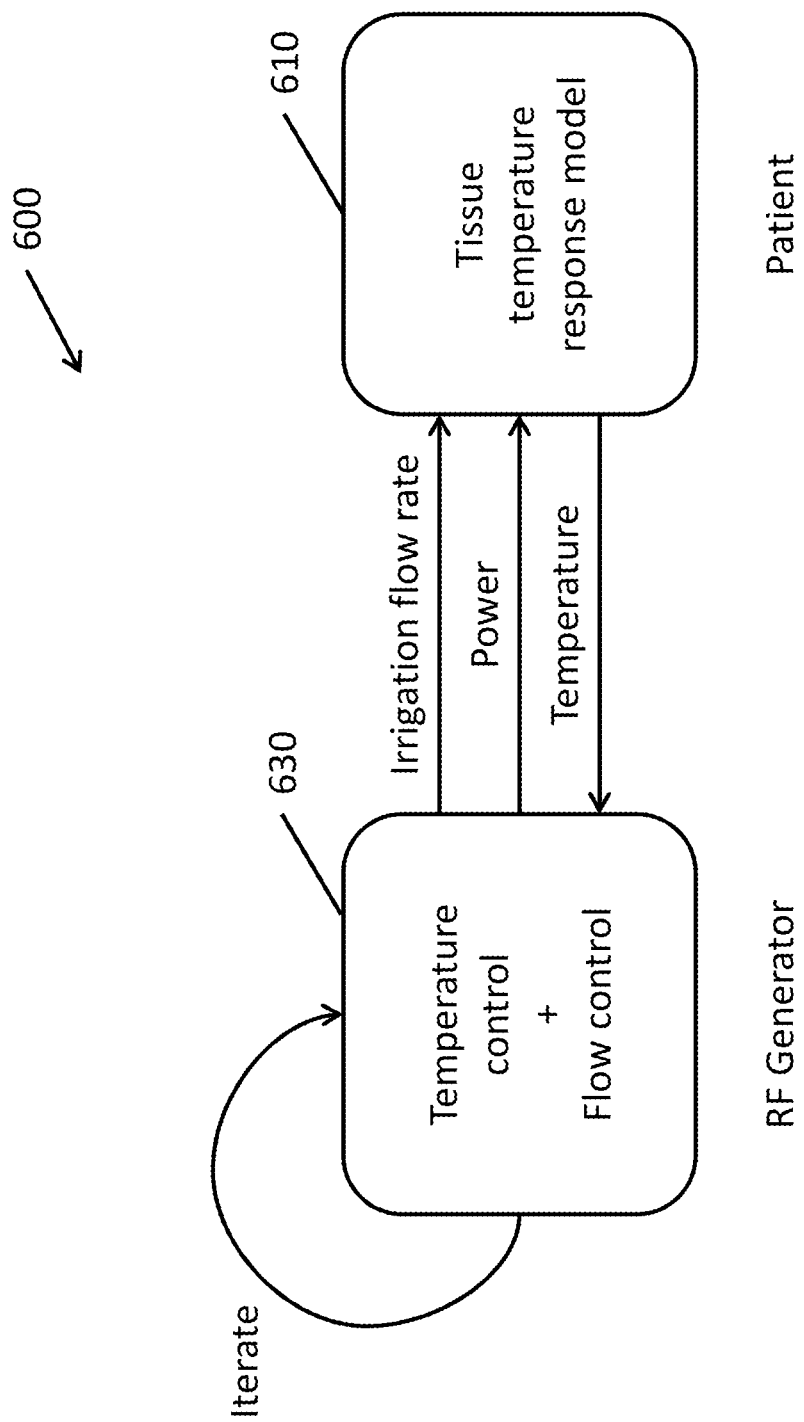
FIG. 6 is a schematic diagram of a simulation framework according to one embodiment of the present invention.

FIG. 6 is a schematic diagram of a simulation framework according to one embodiment of the present invention. As shown in FIG. 6, the framework 600 includes the patient tissue temperature response model 610 described above and a model of a radiofrequency generator model 630. The RF generator model 630 is configured with a target power and a target temperature, and generates output irrigation flow rates and output RF powers. These flow rates and RF powers are supplied to the tissue temperature response model 610, which generates a temperature response that is supplied back to the RF generator model 630. The RF generator model 630 uses the received temperature to update its irrigation flow rate and power output accordingly (e.g., using the techniques of the comparative ablation systems).

The parameters or coefficients of the above formulas for operations 510 and 530 were derived, in one embodiment, by calculating statistical distributions of the model parameters from the available real world data (e.g., animal study data). These distributions are then stretched (e.g., parameters are adjusted) to increase the likelihood that uncommon circumstances that were not measured in the real world data are better represented in the simulated data. A large number of simulated ablations are then performed using a Monte Carlo technique by randomly sampling sets of parameters from the stretched statistical distributions of the parameters and "measuring" the steady state temperatures resulting from those parameters. In one embodiment, for each simulation, the simulated ablation began with an initial flow rate and later switched to another flow rate in order to collect simulated data for fitting the model for calculating an initial flow (corresponding to operation 510) and for fitting the model for calculating an adjusted flow (corresponding to operation 530).

According to one embodiment of the present invention, the steady state thermal energy $E_0$ of the tissue mass at body temperature calculated in accordance with the equation:

$$E_0 = C \cdot m(273+T_0)$$

where $T_0$ is the tissue steady state temperature, m is the effective tissue mass affected by the ablation (assumed to absorb most of the energy as heat), and C*m is the heat capacity of tissue mass m in Joules/Kelvin.

In one embodiment, the energy state of the system at time n in the simulation is calculated based on the following formula:

$$E[n]=E[n-1]+P[n]\Delta t-\alpha(E[n-1]-E_0)\Delta t-\beta C_s F[n]\Delta t(T[n]-T_r)$$

where $E[n-1]$ is the energy state at time n−1, $P[n]\,\Delta t$ is the energy delivered during $\Delta t$ seconds (the time, in seconds, between steps n and n−1), $\alpha(E[n-1]-E_0)\Delta t$ is the energy lost to the environment during $\Delta t$ seconds due to heat transfer (without irrigation), and $\beta C_s F[n]\Delta t(T[n]-T_r)$ represents energy lost to irrigation, where $\beta$ is the irrigation efficiency coefficient, $C_s$ is the heat capacity of the irrigation fluid (e.g., saline), $F[n]$ is the flow rate (m L/sec) at time n, $T[n]$ is the tissue temperature (Kelvin), and $T_r$ is the temperature (Kelvin) of the fluid (e.g., room temperature).

In the above equation, $\alpha$ represents a tissue heat transfer rate, which is a function of catheter tip effective area, blood flow, tissue properties, and the like, and therefore will vary over time in dynamic systems. For a more realistic model, in some embodiments, $\alpha$ is modeled as a stochastic process (bandwidth limited white noise with mean $\alpha_0$, standard deviation a, and low pass cut off frequency $f_0$).

In one embodiment, the instantaneous temperature $T[n]$ is updated in accordance with the formula:

$$T[n] = [n-1] + \frac{1}{C_m}(E[n] - E[n-1])$$

FIGS. 7A, 7B, and 7C are graphs illustrating the simulated performance of irrigation control methods according to embodiments of the present invention. FIG. 7A is a simulation in which the target power is set to 35 W and a target temperature is set at 47° C., and a maximum temperature of 50° C. As shown in FIGS. 7A, 7B, and 7C, the measured temperatures are relatively stable over time when compared to the oscillating temperatures of the comparative examples shown in FIGS. 3A, 3B, and 3C. Furthermore, as shown in FIGS. 7A, 7B, and 7C, temperature control is achieved while keeping the power output constant and with relatively small changes in irrigation flow rates. As a result, adaptive irrigation flow control according to embodiments of the present invention enable improved temperature stability and improved usability for physicians due to more predictable (e.g., linear) responses by the control system to changes in operating parameters (e.g., output power) and environmental changes (e.g., changes in the quality of tip contact).

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. An irrigation system for providing irrigating flow through a catheter probe that is configured for ablating tissue, the irrigation system comprising:
   an irrigation controller configured to supply an irrigation fluid at an irrigation flow rate through the catheter probe, the irrigation flow rate being adjustable in increments of less than or equal to 2 milliliters per minute; and
   an operating console having a processor and memory, the memory storing instructions that, when executed by the processor, cause the processor to control the irrigation controller to set the irrigation flow rate based on a target power delivered by a RF power generator configured for delivering RF power for ablating the tissue and a target average temperature, wherein the memory of the operating console further stores instructions that, when executed by the processor, cause the processor to control the irrigation controller to set the irrigation flow rate to an initial irrigation flow rate during a preablation time based on the target power and the target average temperature, and wherein the memory of the operating console further stores instructions that, when executed by the processor, cause the processor to control the irrigation controller to set the irrigation flow rate to an adjusted flow rate during a power ramp up period after the preablation time, the adjusted flow rate being set based on:

the target power;
the target average temperature;
the initial irrigation flow rate;
a temperature slope during the preablation time, measured by a temperature sensor;
a temperature slope during the power ramp up period, measured by the temperature sensor; and
a temperature rise measured since a start of ablation, measured by the temperature sensor.

2. The irrigation system of claim 1, wherein the memory of the operating console further stores instructions that, when executed by the processor, cause the processor to control the irrigation controller to set the irrigation flow rate to an irrigation flow rate selected from more than two different irrigation flow rates.

3. The irrigation system of claim 1, wherein the memory of the operating console further stores instructions that, when executed by the processor, cause the processor to control the irrigation controller to set the irrigation flow rate by a continuously variable amount.

4. The irrigation system of claim 1, wherein the memory of the operating console further stores instructions that, when executed by the processor, cause the processor to control the irrigation controller to set the irrigation flow rate to a value within a continuous range.

5. The irrigation system of claim 1, wherein the memory of the operating console further stores instructions that, when executed by the processor, cause the processor to control the irrigation controller to set the irrigation flow rate using a proportional-integral-derivative control loop based on a current temperature and the target average temperature.

6. The irrigation system of claim 1, wherein the target average temperature is constant with respect to the target power.

7. The irrigation system of claim 1, wherein the target average temperature is set to increase linearly with respect to the target power.

8. A method for controlling an irrigation system for providing irrigating flow through a catheter probe that is configured for ablating tissue, the method comprising:

providing an irrigation controller of the irrigation system, the irrigation controller configured to supply an irrigation fluid at an irrigation flow rate through the catheter probe, the irrigation controller being configured to control the irrigation flow rate in increments of less than or equal to 2 milliliters per minute, receiving, by an operating console, a target power delivered by a RF power generator configured for delivering RF power for ablating the tissue and a target average temperature, the operating console being configured to receive signals from a temperature sensor and to control the irrigation controller;

controlling, by the operating console, the irrigation controller to set the irrigation flow rate based on the target power and the target average temperature;

controlling the irrigation controller to set the irrigation flow rate to an initial irrigation flow rate during a preablation time based on the target power and the target average temperature; and controlling the irrigation controller to set the irrigation flow rate to an adjusted flow rate during a power ramp up period after the preablation time, the adjusted flow rate being set based on:

the target power;
the target average temperature;
the initial irrigation flow rate;
a temperature slope during the preablation time, measured by the temperature sensor;
a temperature slope during the power ramp up period, measured by the temperature sensor; and
a temperature rise measured since a start of ablation, measured by the temperature sensor.

9. The method of claim 8, further comprising controlling the irrigation controller to set the irrigation flow rate to an irrigation flow rate selected from more than two different irrigation flow rates.

10. The method of claim 8, further comprising controlling the irrigation controller to set the irrigation flow rate by a continuously variable amount.

11. The method of claim 8, further comprising controlling the irrigation controller to set the irrigation flow rate to a value within a continuous range.

12. The method of claim 8, further comprising controlling the irrigation controller to set the irrigation flow rate using a proportional-integral-derivative control loop based on a current temperature measured by the temperature sensor and the target average temperature.

13. The method of claim 8, wherein the target average temperature is constant with respect to the target power.

14. The method of claim 8, wherein the target average temperature is set to increase linearly with respect to the target power.

* * * * *